United States Patent [19]

Crawford et al.

[11] 4,009,313
[45] Feb. 22, 1977

[54] ENZYMATICALLY DISPERSIBLE NON-WOVEN WEBS

[75] Inventors: George H. Crawford, Dellwood; Charles F. Nawrot, Eau Claire; Ronald F. Ofstead, Maplewood, all of Minn.

[73] Assignee: Minnesota Mining and Manufacturing Company, St. Paul, Minn.

[22] Filed: Aug. 30, 1972

[21] Appl. No.: 285,084

[52] U.S. Cl. ............................. 428/290; 128/284; 128/287; 128/290 W; 260/DIG. 43; 428/291

[51] Int. Cl.$^2$ ............... B32B 27/04; B32B 27/10

[58] Field of Search .......... 117/140 A, 140 R, 164, 117/165; 128/284, 287, 290 W; 260/DIG. 43, 8, 17.4 GC; 220/DIG. 30; 428/290, 291

[56] References Cited

UNITED STATES PATENTS

| | | | |
|---|---|---|---|
| 1,761,111 | 6/1930 | Doty | 220/DIG. 30 |
| 3,034,922 | 5/1962 | Boe | 128/284 UX |
| 3,444,859 | 5/1969 | Kalwaites | 128/284 |
| 3,507,661 | 4/1970 | Ofstead | 117/164 X |
| 3,532,647 | 10/1970 | Ritson et al. | 117/140 A |
| 3,619,236 | 11/1971 | Dappen et al. | 117/164 X |
| 3,651,210 | 3/1972 | Shepler et al. | 117/164 X |
| 3,706,595 | 12/1972 | Drelich et al. | 117/140 A |

*Primary Examiner*—Harry J. Gwinnell
*Attorney, Agent, or Firm*—Alexander, Sell, Seldt & DeLaHunt

[57] ABSTRACT

A self-supporting, non-woven composite web is described which is readily dispersible in aqueous media containing enzymes. The web comprises intersecting randomly or partially oriented fibers and has low wet-strength in the absence of a binder, the fibers being bonded in web form by a polymeric binder which is attacked and disintegrated by enzymes, thus permitting the fibers to disperse rapidly in aqueous milieu containing enzymes. The webs of the invention are useful for production of articles useful for absorbing body wastes, e.g. diapers, bandages, etc.

17 Claims, No Drawings

ENZYMATICALLY DISPERSIBLE NON-WOVEN WEBS

BACKGROUND OF THE INVENTION

Non-woven fabrics have gained wide acceptance for use in disposable products because of their relatively low cost of manufacture as compared to that of more conventional fabrics made by weaving or knitting processes. They have a wide variety of uses including surgical dressings, incontinence pads, diapers, cigarette filters, quilting or padding, cleaning materials and the like. Such non-woven fabrics are commonly available commercially in a wide range of fabric weights from as little as about ten grams per square meter to as much as about 200 or more grams per square meter.

These items require greater or less dry- and wet-strength according to the use for which they are designed. Extremely low strength materials such as those used for facial cleansing tissues often are required to have substantially no wet-strength. Other items such as bandages should have relatively high dry- and wet-strength to permit use over a period of time in the presence of body fluids or water.

The disposal of these non-woven products, particularly those employed for sanitary purposes and involving containment of body wastes, often has been a problem. Disposal of these items into sewage systems through the restrictive passages of sanitary plumbing may cause clogging. Incineration of such items, particularly where frequent use is necessary and therefore accumulation of considerable amount of disposable material occurs, as in the use of disposable diapers, may also be unsatisfactory.

Various non-woven fabrics have been designed for use in sanitary absorbent products such as diapers and the like which are designed to disintegrate or disperse when the product is placed in water, as in the household toilet. In an effort to provide non-woven fabrics which retain their integrity in the presence of more than limited quantities of aqueous fluids, yet allowing for dispersal of the fibers of the web when this is placed in water, a number of bonding methods have been proposed. Intermittent or random patterns of adhesive or binder resin to bind fibers is disclosed in U.S. Pat. Nos. 2.039,312 and 3,616,797, and other patents; use of stitching is disclosed in U.S. Pat. NO. 2,010,433; use of water-soluble binders in U.S. Pat. Nos. 2,999,038; 3,310,454; 3,370,590; 3,546,716 and 3,554,788 and possibly others; and the use of water-soluble fibers as such is disclosed in e.g. U.S. Pat. Nos. 3,347,236 and 3,550,592. In U.S. Pat. No. 3,480,016 there is described an absorbent product which is water-disperible when an acid or alkali is added to the water, in which a random web of non-woven fibers is bound by means of an acid or alkali sensitive binder.

The water-dispersible product of the prior art, as disclosed in the above-mentioned patents, are not entirely satisfactory for the purposes designed. Some of them are inherently disintegratable in the presence of water, thus maintaining their integrity only in the presence of limited quantities of aqueous fluids. The non-woven products of U.S. Pat. No. 3,480,016, although seemingly stable in water alone, are apparently to a degree unstable in acidic or basic aqueous systems which have pH in the range of that of physiological (body) fluids. In any case it appears that it requires use of added acid or base to disposal systems for effective dispersal of these webs.

While the use of acid- or base-sensitive binders for non-woven webs, which permits disposal after disintegration by means of an acidic or basic reagent, appears to present the best solution thus far advanced for the problem of disposable absorbent materials, this approach is still not believed to be practical. The repeated use of acids or alkalis, whether dilute or concentrated, is believed to be detrimental in the long run to sewage disposal systems depending upon natural organisms for degradation and disposal of sewage. Further, if large numbers of people were to employ such materials in conjunction with municipal disposal systems involving a large central treating station, it is believed that problems would arise in connection with accumulation of acidic or basic materials at some point in the system. Moreover, there is personal hazard inherent in such processes, in the handling, storage and use of the irritating or hazardous chemical reagents required to bring about disintegration of the binders in the aqueous solutions.

BROAD DESCRIPTION OF THE PRESENT INVENTION

This invention relates to a non-woven web or fabric which has significant wet-strength when wet by or immersed in water, but which is rapdily dispersed or disintegrated into its individual fibers when placed in water containing enzymes capable of degrading or otherwise affecting or solubilizing a polymeric binder which is applied to the web, and which is thereby readily disposable in sewage systems. The invention further broadly relates to a process for rapid disintegration or dispersion of absorbent, non-woven webs used for sanitary purposes, in connection with standard sewage systems under conditions which do not upset processes to which the sewage is normally subjected.

It is an aim of the invention to provide non-woven fabrics which are inexpensive, possess sufficient wet-strength to maintain their integrity under all conditions of use, but which are rapdily, easily and safely disposed of in an aqueous system. A further aim of the invention is to provide non-woven web and process for disposal thereof which enables use of these items in domestic sewage and septic systems with frequent and repetitive use without clogging plumbing passageways or interfering with natural process of disposal.

In accordance with the object of the invention, there is provided a self-supporting, non-woven composite web which is readily dispersible in aqueous milieu containing enzymes, which web consists essentially of a non-woven web of short fibers having surfaces which confer only low wet-strength upon the web in the absence of a binder, but which are according to the invention combined with a water-insoluble, normally solid enzyme-disintegratable binder which is sufficient to impart to the non-woven web a wet-strength in water in the absence of enzyme of from about 0.7 to 10 kg. per square centimeter. The non-woven web-binder composite is dispersible in a period ranging from about five to about 30 minutes in an aqueous milieu containing enzyme capable of disintegrating the binder.

Preferably, the composite webs of the invention are resistant to dispersion in water free from enzyme for periods greater than about 30 minutes. The dry-strength of these materials is generally greater than their wet-strength, and is preselected so as to be commensurate with the use for which they are designed. The wet-strength, however, is pre-selected to fall within the range of about 0.7 to about 10 kg. per square centimeter, as that range encompasses substantially all of the uses to which the articles of the invention are likely to be put.

The non-woven webs useful in the practice of the invention are prepared by carding, garnetting, air deposition, water deposition or any of the various techniques known in the art for the purpose. The fibers may be oriented predominantly in one direction as in a card web or card web laminate, if desired. Alternatively, they may be substantially isotropic, that is they may have equivalent strength in all dirctions. Useful fibers for the purpose are those of viscose rayon, cotton, wool, silk, cellulosics, linen, hemp, wood fibers and the like, or purely synthetic fibers, e.g. regenerated cellulose, nylon, polyester, etc.

Preferred fibers for the purpose of the invention are natural fibers which are ultimately biodegradable. The length of fiber that can be employed is not critical, but is is preferred to use relatively short fibers, i.e. those having length between about three to about 12 millimeters. The non-woven webs thus produced can have a weight of the order of about ten to 100 or more grams per square meter depending upon the end use. For example, a weight of about 20 to 60 grams per square meter is preferred for use as a diaper liner.

A convenient method for producing the non-woven webs is by any of various techniques known to the art, such as carding, garnetting, air deposition, water deposition and the Fourdrinier process as in paper making. If desired, the web can be calendered to a smooth, hard finish.

The binder employed in the invention is a water-insoluble polymer of at least one ethylenically unsaturated monomer, covalently bonded with a naturally-occurring, enzyme-degradable, water-soluble polymeric material. Exemplary of such are the reaction products with gelatin disclosed in U.S. Pat. No. 3,507,661. The polymers reacted with gelatin in these binders have a molecular weight of at least 10,000 and a degree of polymerization of at least 50, and preferably are of a molecular weight such that they have glass transition temperature ($T_g$) which is substantially independent of the molecular weight of the polymer.

The ethylenically unsaturated polymer can also be termed a vinyl polymer. The polymers employed are required to have substituent groups, either pendant or terminal, which are reactive with the water-soluble, naturally-occurring polymers. Such vinyl polymers are polymers and copolymers of addition-polymerizable vinyl monomers which have substituent groups reactive with compounds having active hydrogen.

The term "active hydrogen" used herein is well known and commonly used in the art, and means active hydrogen as measured and determined by the method described by Zerewitinoff, J. Am. Chem. Soc. 49, 3181 (1927).

Illustrative of the ethylenically unsaturated (vinyl) polymers and copolymers of addition-polymerizable vinyl monomers useful in the practice of the invention are those polymers having repeating vinyl or vinylidine units, at least one mol percent and preferably from five to 30 mol percent of which contain one or more groups reactive with active hydrogen atoms. Although the molecular weight of these polymers can vary over a wide range, they generally speaking have a molecular weight ranging from about 1,000 to several million or more. A preferred class of copolymers are those that have a molecular weight such that the glass transition temperature ($T_g$) is substantially independent of the molecular weight, as described in J. Poly. Sci. 3A, 3579 (1965).

These vinyl polymers can be homopolymers or copolymers in which vinyl monomers having reactive substituent groups are copolymerized with vinyl monomers which do not have reactive subsitituent groups. Exemplary of monomers providing reactive substituent groups for the purpose are those including epoxy-containing monomers, e.g. glycidyl acrylate, glycidyl methacrylate and 3,4-epoxybutene-1; N-methylol amide monomers, e.g. N-methylol acrylamide, N-methylol methacrylamide; aldehyde-containing monomers, e.g. acrolein, methacrolein or acetals or bisulfite addition products thereof and methyl vinyl ketone; alpha-haloesters, e.g. vinyl alpha-chloroacetate and aziridine-containing monomers, e.g. N-allyl aziridine and acryloxyalkylaziridine; and anhydrides, e.g. maleic anhydride. Vinyl monomers that may be employed in the preparation of copolymers with monomers containing a reactive substituent group include acrylate esters, e.g. methyl acrylate, ethyl acrylate, methyl methacrylate, butyl acrylate and 2-ethylhexyl acrylate; vinyl esters, e.g. vinyl acetate, vinyl propionate; olefins, e.g. ethylene, propylene, styrene, vinyl cyclohexene; dienes, e.g. 1,3-butadiene, isoprene, chloroprene; vinyl ethers, e.g. methyl vinyl ether, butyl vinyl ether and octadecyl vinyl ether; amides, e.g. acrylamide, methacrylamide, vinyl pyrrolidone; and acrylonitrile. Since the preparation of polymers and copolymers of the above monomers is extensively described in the literature, further elaboration is not necessary for a complete understanding of this invention. U.S. Pat. No. 3,242,123, for example, provides an illustration of the preparation of copolymers useful in the practice of this invention. The reactive polymers generally are prepared in solution in an organic solvent or in emulsion and are utilized as such in the preparation of the enzyme-degradable binders used in the practice of this invention.

The naturally-occurring, water-soluble, enzyme-degradable polymers which are reacted with (covalently bonded with) the above vinyl polymers to form the enzyme-disintegratable binder for use with the non-woven web contain active hydrogen groups in their structure, which can react convalently with the vinyl polymers because they have one or more imide, amide, amino, hydroxyl or carboxyl groups in their structure. They may be soluble in water to form a true solution, but in some cases for a sol or colloidal solution. The use of the term "water soluble" herein in connection with these naturally-occurring polymers is intended to refer to both true solutions and collodial solutions. They are commonly capable of forming self-supporting films by evaporation of water solutions of the polymer.

Exemplary of such naturally-occurring polymers which are useful in the preparation of the binder used in the non-woven web composite of the invention are included both animal and vegetable proteins such as, for example, albumins, e.g. serum albumin, egg albumin, ricin, leucosin and legumelin; globulins, e.g. serum globulin, myosin and myogen from muscle, edestin from hemp, and grain globulins; prolamines, e.g. zein, hardein from barley, and gliadin from wheat; glutelins, e.g. gluetenin from wheat and maize, and oryzein from rice; protamines, e.g. salmin and culpein; scleroproteins, e.g. collagen, gelatin, animal glue, elastin and fibroin; phosphoproteins, e.g. casein and vitellin; and glyco-proteins, e.g. mucins, mucoids and ovalbumin.

Examples of film-forming polysaccharides that may be used as the enzyme-degradable polymer component of the enzyme-disintegratable binder for the fibers in the non-woven fabric of the invention include starch, glycogen, inulin, amylose; amylopectin; the seaweed polysaccharides, e.g. algin, propylene alginate and other algin derivatives, carrageenan, fucoidan, luminaron and agar; the exudate gums, e.g. gum arabic, gum ghatti, gum karaya, tamarind gum and tragacanth gum; and other gums, e.g. locus bean gum, guar gum and pectin.

In the preparation of the actual reaction product which constitutes the enzyme-dispersible binders employed in this invention, a binder-forming formulation is first prepared. The binder-forming formulation is prepared by blending an organic or aqueous solution, dispersion or emulsion of the reactive group-substituted polymer with a solution or dispersion of the enzyme-degradable polymer. The binder-forming formulation is then applied to a non-woven web and the solvents removed, whereon the reaction between the reactive group-substituted polymer and the enzyme-degradable takes place to form in situ the reaction product which constitutes the enzyme-dispersible binder. For example, an enzyme-dispersible binder-forming formulation suitable for use as a binder for the enzyme-dispersible, non-woven webs of the invention is prepared by mixing eight parts by weight of a 15 percent aqueous emulsion of an ethyl acrylate/glycidyl methacrylate copolymer (80/20 mol ratio), prepared as described in Example 1 of U.S. Pat. No. 3,507,661, with 92 parts of a 13.5 percent aqueous solution of collagen. The aqueous formulation of reactive group-substituted polymer and enzyme-degradable polymer is then used to prepare the enzyme-dispersible, non-woven fabrics of the invention.

The enzyme-disintegratable binder-forming formulation is applied to the non-woven web to prepare the fabrics of the invention by various processes known to the art, such as, for example, by spraying a solution, emulsion or dispersion of the enzyme-dispersible binder onto the non-woven web; by dipping the non-woven web into a solution, emulsion or dispersion of the enzyme-dispersible binder; or by transfer rolling the solution, emulsion or dispersion to the web. The binder-forming formulation may also be applied to the web during water deposition as in the Fourdrinier process, wherein the binder emulsion or dispersion is added to the process water.

After application of the binder to the web, the web is allowed to dry, whereon reaction of the reactive groups of the reactive group-substituted polymer and the enzyme-degradable polymer takes place with the formation of covalent bonds. This reaction may be accelerated by drying the wet web at elevated temperatures, e.g., 40°–70° C., for a short time. Generally, the concentration of enzyme-disintegratable binder in the solution, emulsion or dispersion is adjusted by addition of fluid, e.g., organic solvent, water or aqueous solutions, so that after application to the non-woven web and drying about 0.3 to about 100 percent, and preferably one to about 15 percent, by weight of the dry web of enzyme-disintegratable binder remains on the web.

The non-woven webs thus formed can have rather high dry tensile strength if desired. Not uncommonly, they have dry tensile strength of the order of 100 to 150 kg./cm$^2$. However, dry-strength in excess of 35 kg./cm$^2$ is generally not required for most purposes for which the absorbent materials of the invention are to be put. Dry-strength accordingly is relatively unimportant for the webs of the invention. However, when immersed in water, the webs of the invention show wet-strength which can range from 0.5 to 10 kg./cm$^2$ or more, depending upon the particular binder which is employed, and the amount of binder which is placed upon the web. Wet-strength is also increased by drying of the wet web and binder at elevated temperatures as set forth above. Preferably wet-strength is 2 to 10 kg./cm$^2$. When wet-strength is very low, the non-woven fabrics may disintegrate in water alone after a period of 30 minutes to 1 hour. However, when wet-strength is higher, it is commonly noted that even after immersion in water for periods of hours or even days, there is very little change in the tensile strength.

For use for various purposes, the webs of the invention are cut, dyed or otherwise shaped to the desired form. They may be folded into multiple layers, etc. In this way, they are conveniently employed for the manufacture of a variety of useful products such as diapers, catamenial bandages, surgical bandages, disposable washcloths, etc. For disposal, they are readily dispersed into fibers merely by placing in the water in which they are to be disposed an amount of enzyme.

Enzymes are water-soluble or colloidal organic catalysts generally produced by living organisms, for example, animals, plants, fungi and bacteria. Enzymes are normally categorized in accordance with the classes of chemical reactions or processes which they are capable of catalyzing. Thus, a wide variety of hydrolases, oxidases, reductases, transferases and isomerases, etc. exist which catalyze chemical processes of hydrolysis, oxidation, reduction, group transfer, isomerization, etc. The presence of water is in most cases required for enzyme catalysis to be operable. Conditions of pH, ionic strength, temperature, etc., as well as the presence of additional chemical substances such as cofactors may also be important in obtaining maximum catalytic effects, depending upon the nature of the individual enzyme and the chemical reaction or process being catalyzed by the enzyme. More complete descriptions of enzymes, their structure and catalytic action are readily available; see, for example, the series of publications "The Enzymes," edited by Paul D. Boyer, Academic Press, New York, or U.S. Pat. No. 3,386,441 which discloses various proteolytic, mucolytic or amylolytic enzymes as applied to catamenial absorbent pads.

Enzymes preferred for the practice of this invention are the hydrolases which catalyze the hydrolysis of a wide range of macromolecular substances to lower molecular weight materials, fragments or units. Hydrolases are relatively innocuous materials, which are used in such common household products as meat tenderizers. Examples of suitable hydrolases are the proteases which catalyze the hydrolysis of proteins to peptides or individual amino acids, e.g., Protease-62 (available from Rohm and Haas Company, hereinafter R and H), Papain, Ficin and Bromelain (available from Miles Laboratories), Trypsin and Chymotrypsin (available from Sigma Chemical Company); polysaccharide hydrolases such as the cellulases which catalyze the hydrolysis of cellulose and many substituted cellulose derivatives to lower molecular weight saccharides, e.g., Cellulase-4000 (available from Miles Laboratories); the pentosanases-hexosanases which catalyze the hydrolysis of gums and mucilages to lower molecular weight polysaccharides and/or sugars, e.g. HP-150 (R nd H); and the diastases which catalyze the hydrolysis of starch to carbohydrates of smaller size and less complexity, e.g. Rhozyme-S, -33 and H-39 (R and H).

The dispersion of the non-woven webs of the invention for disposal purposes is accomplished by simply wetting the fabric with water containing a suitable enzyme or, possibly more conveniently, by placing the fabric water and adding thereto a suitable enzyme for disintegration of the binder. The enzyme concentration which is most effective will naturally vary according to the enzyme used and its particular activity upon the binder. The particular enzyme used may require buffered conditions, and this may be accomplished e.g. by including in the dry enzyme preparation an amount of dry buffering agent.

Using, for example, a somewhat crude enzyme preparation known and available commerically as Protease-62 (a protease catalyzing the hydrolysis of proteins to peptides or individual amino acids), the useful concentration of enzyme in water can vary from about 0.1 to about 0.5 percent, or higher if desired. Preferably the concentrations employed are about 0.05 to about 0.15 percent, whereby disintegration and dispersion of the webs is fast enough from a practical standpoint. Thus, an amount of about 1.5 to 3 grams of enzyme is sufficient for use with the average domestic toilet (about 3 liters of water) for each disposal of a diaper, for example. Obviously the use of too much enzyme is wasteful as the corresponding increase in dispersion of the web is not directly proportional to the amount used.

In this way, items made of the composite webs of the invention can be employed for various sanitary purposes and disposed of in ordinary domestic septic tank-type sewage disposal systems without the use of dangerous and irritating substances, and without causing deleterious effects upon the said systems. Frequently repeated use does not cause build-up of undesirable materials in the said disposal systems. At the same time, the enzymes employed may have a deodorizing or disintegrating effect upon the human wastes which are absorbed, which is also advantageous.

Usefully, an enzyme preparation in dry, powdered form is associated with the sanitary item, as by placing it in a fold or pocket thereof which does not become wet during use. Thus disposal in aqueous milieu conveniently requires no separate addition of enzyme. Other such combination of enzymes with the articles made of the non-woven webs of the invention will readily suggest themselves.

The following examples will serve to illustrate production of some specific embodiments of the invention. Parts are by weight unless otherwise specified.

EXAMPLE 1

A non-woven web is produced in a 20 × 20 cm. laboratory model paper sheet former using 4 liters of water and 100 ml. of a dispersion prepared by mixing in a high speed blender 19 parts of 6 mm. RD101 Viscose Rayon Fibers (available from American Viscose Company) and 1900 parts of water containing 0.4 part of Triton X-100 surfactant (alkylaryl polyether alcohol available from Rohm and Haas Company). After dispelling the water, the sheet formed on the screen is removed on a 20 × 20 cm. piece of blotting paper and dried at 80° C. It has a weight of 24 grams/meter$^2$.

An aqueous dispersion of an enzyme-disintegratable binder is prepared by mixing 5 parts of a 15 percent emulsion of an ethyl acrylate/glycidyl methacrylate copolymer (90/10 mol ratio) (prepared as described in Example 1 of U.S. Patent 3,507,661) with 0.75 part of collagen (e.g. Technical Protein Colloid No. 5-V, available from Swift and Company) dissolved in 55 parts of warm distilled water adjusted to pH 7.0 to 7.2 with 0.1 N sodium hydroxide solution.

The 20 × 20 cm. non-woven web as prepared above is sprayed with 20 ml. of the aqueous dispersion, allowed to dry at room temperature for one hour and then heat cured at 70° C. for 2 hours. The dried non-woven fabric obtained has a tensile strength of approximately 263 kg./cm$^2$. Wet-strength is in the range of 4.7 kg./cm$^2$. Samples of the web when placed in a 0.1 percent solution of Protease-62 (a bacterial enzyme available from Rohm and Haas Company) buffered to pH 8 and agitated to and fro at room temperature on a mechanical shaker are completely dispersed in 10 to 15 minutes. Samples of the web when agitated in an aqueous solution at pH 8 and room temperature but not containing enzyme required 45 to 75 minutes for dispersal.

The non-woven web before application of enzyme-disintegratable binder has a tensile strength of about 80 kg./cm$^2$ when dry, and when wet with water, the web falls apart completely.

When samples of the fabric prepared as in Example 1 are agitated in a 0.1 percent solution of Enzyme 56-lot 1 (R and H protease) buffered to a pH of 10, the web disperses completely in 10 minutes at room temperature. Comparable times are also obtained with Enzyme P-53 and Enzyme B-6 (both protease, R and H).

EXAMPLE 2

A non-woven web is prepared from repulped paper in accordance with the procedure described in Example 1. The non-woven web has a weight of 40 grams/meter$^2$ and disperse immediately on contact with water.

A dispersion of an enzyme-dispersible binder is prepared by mixing an emulsion containing 3.19 g. of an ethylacrylate/glycidyl methacrylate copolymer (90/10 mol ratio, prepared as described in Example 1 of U.S. Pat. No. 3,507,661) in 500 ml. of water with a solution of 3.0 g. of gelatin in 500 ml. of water adjusted to pH 7.5.

The non-woven web from repulped paper is sprayed to saturation with the above-described enzyme-dispersible binder and air dried. After drying, the treated web is heated in an oven at 40° C. for 3 hours. Weight gain is less than 1 percent. The bonded non-woven fabric obtained has a dry tensile strength of approximately 133 kg./cm$^2$. Wet-strength is from 2.8–3.5 kg./cm$^2$. Samples of the enzyme-dispersible binder treated fabric when placed in a 0.1 percent solution of Enzyme 56-lot 1 at pH 10 and room temperature and agitated on a mechanical shaker are completely dispersed in 10 minutes. Comparable dispersion times are also obtained using Enzyme P-53 and Enzyme B-6.

EXAMPLE 3

Example 1 is repeated using as the enzyme-dispersible binder an aqueous dispersion prepared by mixing 500 ml. of an aqueous emulsion adjusted to pH 7.5 and containing 2.85 g. of an ethyl acrylate/acrolein copolymer (90/10 mol ratio) with 500 ml. of an aqueous solution containing 3.1 g. of acacia (gum arabic) adjusted to pH 7.5.

The ethyl acrylate/acrolein copolymer used above is prepared by a method analogous to that used for the preparation of ethyl acrylate/glycidyl methacrylate copolymer described in Example 1 of U.S. Pat. No. 3,507,661 using in place of glycidyl methacrylate an equivalent amount of acrolein.

The non-woven fabric prepared in accordance with this example disintegrates completely in about 15 minutes when agitated on a mechanical shaker in a 0.1 percent solution of HP-150-mixture 144 (a diastase, R and H).

EXAMPLE 4

A 20 × 20 cm. non-woven viscose fiber web prepared as described in Example 1 is sprayed with 20 ml. of an emulsion prepared by mixing a solution of 0.75 g. of hide glue in 55 ml. of water with 5 ml. of a 15 percent solids latex of a 90/10 ethyl acrylate/glycidyl methacrylate copolymer as described in Example 1. The treated fabric is dried at room temperature for 18 hours and then cured by heating at 75° C. for 1 hour.

Samples of the non-woven fabric obtained disintegrate completely in 12 to 16 minutes on a mechanical shaker in 0.1 percent solution of Protease-62 that is buffered at pH 9. When agitated in water at pH 9 in the absence of enzyme, 60 to 90 minutes are required to disintegrate the fabric.

EXAMPLE 5

A 20 × 20 cm. non-woven viscose fiber web prepared as described in Example 1 is sprayed with 10 ml. of a 1 percent solution of gelatin (culture media grade) in water adjusted to pH 7. The gelatin-treated web is air dried and then heated at 60°–65° C. for 1 hour. The dried web is then given a second spraying with 5 ml. of a 1 percent solution of a 65/25/10 methyl methacrylate/ethyl acrylate/glycidyl methacrylate terpolymer (prepared by suspension polymerization according to procedures well-known in the art) in solvent. The terpolymer-treated web is air dried and then cured by heating with a hot iron at 100° C. for 60 seconds.

The bonded non-woven fabric prepared as above has a tensile strength of 187 kg./cm². Wet tensile strength is about 5.2 kg./cm². When agitated in 0.1 percent solution of Protease-62 in tap water, samples of the fabric are dispersed in 3 to 6 minutes. When agitated in water without enzymes, dispersal time is about 70 minutes.

EXAMPLE 6

Bonded non-woven webs are prepared in accordance with the procedure described in Example 5 with the exception that for the second spraying, 5 ml. of a 1 percent solution in acetone of a styrene/maleic anhydride copolymer having a molecular weight of about 1000 is used in place of the terpolymer solution. The web is then air dried and cured by heating with a hot iron at 100° C. for 60 seconds.

The bonded non-woven fabric obtained has a dry tensile strength of 237 kg./cm² and a wet tensile strength of 8.4 kg./cm². In 0.1 percent solutions of Protease-62 in tap water, samples of the fabric are dispersed in 6 to 10 minutes. In water without enzymes, dispersal time is from 2 to 6 hours.

EXAMPLE 7

When Example 6 is repeated using a 1 percent solution in acetone of a methylvinylether/maleic anhydride copolymer (Gantrez AN-119) in place of the 1 percent acetone solution of styrene/maleic anhydride copolymer, the non-woven fabric obtained disperses in 11 to 20 minutes when agitated in 0.1 percent solutions of Protease-62. Dispersal time when agitated in water without enzymes is from 2 to 3 hours.

EXAMPLE 8

Preparation of 90/10 vinyl pyrrolidone/glycidyl methacrylate copolymer.

A 3-neck, round bottom flask equipped with a mechanical stirrer, means for maintaining an inert atmosphere, and a thermometer is charged with 395 ml. of distilled water, 22.2 g. (0.2 mol) of N-vinyl pyrrolidone, and 3.10 g. (0.022 mol) of glycidyl methacrylate. The flask is flushed with nitrogen, and the contents are maintained under nitrogen during the course of the reaction. The mixture is stirred, the temperature raised to 50–55° C. and maintained at this temperature, and 0.2 g. of 4,4'-azobiscyanopentanoic acid is added as polymerization catalyst. As solid material separates from solution during the reaction, acetone (totaling 125 ml.) is added to maintain it in solution. Agitation and heating is maintained for a total of about three hours. At the end of this time the mixture is cooled, and the colorless, syrupy solution is filtered to remove a small amount of insoluble material. The solution obtained contains about 5 percent copolymer. It may be used as such or the polymer may be isolated by spray or drum drying.

EXAMPLE 9

A non-woven web, prepared as in Example 1, is sprayed with 20 ml. of an aqueous solution adjusted to pH 7 of 1 g. of hide glue and 1 g. of a 90/10 N-vinyl pyrrolidone/glycidyl methacrylate copolymer (prepared as described in Example 8) in 200 ml. of water. The treated web is air dried and cured by heating with a hot iron at 100° C. for 30 seconds. When agitated in 0.1 percent solutions of Protease-62 in water, the dispersal time is 12 to 14 minutes. When agitated in water without enzyme, dispersal time is 50 to 65 minutes.

EXAMPLE 10

Preparation of 90/10 vinyl pyrrolidone/acrolein copolymer.

A 3-neck, round bottom flask equipped with a mechanical stirrer, means for maintaining an inert atmosphere in the flask and a thermometer is charged with 368 ml. of distilled water, 22.2 g. (0.2 mol) N-vinyl pyrrolidone and 1.3 g. (0.02 mol) of acrolein. The flask is flushed with nitrogen, and the contents of the flask are maintained under nitrogen during the course of the reaction. The mixture is stirred, the temperature is raised to 50°–55° C. and maintained at this temperature, and 0.2 g. of 4,4'-azobiscyanopentanoic acid is added. After 2 hours reaction an additional 0.2 g. of 4,4'-azobiscyanopentanoic acid is added, and the reaction is allowed to continue for an additional 3 hours. At the end of this time, the mixture is filtered to remove a small amount of insoluble material. The filtrate obtained contains about 6 percent by weight of copolymer. The solution may be used as such or isolated by spray or drum drying.

EXAMPLE 11

Example 7 is repeated using 1 g. of 90/10 N-vinyl pyrrolidone/acrolein copolymer (prepared as described in Example 10) in place of 1 g. of 90/10 N-vinyl pyrrolidone/glycidyl methacrylate copolymer.

The non-woven fabric obtained has a dispersal time in aqueous one percent Protease-62 solution of 4 to 5 minutes. In the absence of Protease-62, the dispersal time in water is greater than 6 hours.

EXAMPLE 12

A non-woven web prepared as in Example 1 is sprayed with 20 ml. of an aqueous solution prepared by dissolving 1 gram of edible grade corn starch in hot water, cooling to room temperature, adding 1 g. of 90/10 N-vinyl pyrrolidone/acrolein copolymer (prepared as described in Example 10) and diluting the mixed solution to 200 ml.

The non-woven fabric obtained has a dispersal time when agitated in aqueous 0.1 percent Protease-62 of 30 to 40 minutes. (Protease-62, a bacterial enzyme preparation, contains only a low diastase or starch-liquefying activity.) When samples of the fabric are agitated in 0.1 percent of Rhozyme-S, a diastase enzyme, the dispersal time is about 12 to 15 minutes. In the absence of enzymes, dispersal time of the fabric is about 60 to 65 minutes.

What is claimed is:

1. A self-supporting, non-woven composite fibrous web which is readily dispersible in aqueous milieu containing enzyme, consisting essentially of a non-woven web of relatively short fibers having surfaces which confer only low wet-strength upon the web in the absence of a binder and in combination therewith a water-insoluble, normally solid, enzyme-disintegratable binder which consists of the reaction product of a polymer containing at least one ethylenically unsaturated monomer covalently bonded with a naturally occurring, enzyme-degradable, water-soluble polymeric material, said binder being present in effective amount ranging from about 0.3 percent to about equal amount by weight of said fibers in said non-woven web, sufficient to impart to said non-woven web wet-strength in the absence of enzyme of from about 0.5 to 10 kg/cm$^2$ and resistance to dispersion in water for at least 30 minutes, and to permit dispersion of said non-woven web in a period ranging from about 5 to 30 minutes in aqueous milieu containing enzyme capable of degrading said water-soluble polymeric material to disintegrate said binder and thereby to render said web dispersible.

2. Composite web according to claim 1, in which the polymer has molecular weight such that the $T_g$ is substantially independent thereof and the binder is present in amount of about 1 to 15 percent by weight of the dry web.

3. Composite web according to claim 1, wherein the enzyme-degradable, water-soluble polymeric material is a protein.

4. Composite web according to claim 1, in which the enzyme-degradable, water-soluble polymeric material is a polysaccharide.

5. Composite web according to claim 1, in which the binder is a polymer of at least one ethylenically unsaturated monomer, which polymer has a molecular weight of at least 10,000 and a degree of polymerization of at least 50, said water-insoluble polymer being covalently bonded directly to gelatin.

6. Composite web according to claim 1, in which the ethylenically unsaturated polymer is a copolymer containing recurring monomer units, from about 5 to about 0460 30 mole percent of said monomer units corresponding to an ethylenically unsaturated monomer having at least one group reactive with naturally-occurring enzyme-degradable, water-soluble polymeric material.

7. Composite web according to claim 6, in which the naturally-occurring polymer is gelatin.

8. Composite web according to claim 1, in which the fibers are viscose rayon fibers.

9. Composite web according to claim 1, in which the fibers are wood pulp fibers.

10. Composite web according to claim 1, in which the binder is ethylacrylate/glycidyl methacrylate copolymer in 90/10 mole ratio covalently bonded with gelatin.

11. Composite web according to claim 1, in which the binder is ethylacrylate/acrolein copolymer in 90/10 mole ratio covalently bonded with gum arabic.

12. Composite web according to claim 1, in which the binder consists of terpolymer of methylmethacrylate/ethylacrylate/glycidyl methacrylate in 65/25/10 ratio covalently bonded with gelatin.

13. Composite web according to claim 1, in which the binder is methyl vinyl ether/maleic anhydride copolymer covalently bonded with gelatin.

14. Composite web according to claim 1, in which the binder is styrene/maleic anhydride copolymer covalently bonded with gelatin.

15. Composite web according to claim 1, in which the binder is N-vinyl pyrrolidone/acrolein copolymer in 90/10 ratio covalently bonded with corn starch.

16. Composite web according to claim 1, containing binder in effective amount of from about 1 to 15 percent by weight of the dry web of fiber.

17. Composite web according to claim 1, having wet-strength in aqueous milieu in the absence of enzyme ranging from about 2 to 10 kg./cm$^2$.

* * * * *